(12) United States Patent   (10) Patent No.: US 8,911,145 B2
Simpson                         (45) Date of Patent:    Dec. 16, 2014

(54) METHOD TO MEASURE THE CHARACTERISTICS IN AN ELECTRICAL COMPONENT

(75) Inventor: Ceber Simpson, Monroe County, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1079 days.

(21) Appl. No.: 12/623,336

(22) Filed: Nov. 20, 2009

(65) Prior Publication Data

US 2011/0122916 A1    May 26, 2011

(51) Int. Cl.
*G01K 11/26* (2006.01)
*G01N 17/00* (2006.01)
*G01N 25/00* (2006.01)
*G01N 25/72* (2006.01)
*G01N 21/64* (2006.01)

(52) U.S. Cl.
CPC ............ *G01N 25/72* (2013.01); *G01N 21/6489* (2013.01); *G01N 2021/646* (2013.01)
USPC .................. 374/57; 374/4; 374/178; 374/162

(58) Field of Classification Search
CPC ..... H01S 3/0675; H01S 53/1628; H01S 3/30; G02F 2202/00; G02F 2200/15
USPC ......... 374/4, 5, 120, 121, 130–132, 141, 178, 374/29, 30, 110, 112, 137, 166, 167, 57, 45, 374/162, 117–119; 250/338.1
See application file for complete search history.

(56) References Cited

U.S. PATENT DOCUMENTS

| | | | |
|---|---|---|---|
| 3,750,182 A | | 7/1973 | Kernweis |
| 3,935,577 A | | 1/1976 | Hansen |
| 4,105,337 A | * | 8/1978 | Bjorklund et al. ............. 356/364 |
| 5,568,978 A | * | 10/1996 | Johnson et al. ................ 374/161 |
| 5,741,070 A | * | 4/1998 | Moslehi ......................... 374/161 |
| 5,984,522 A | * | 11/1999 | Koizumi ............................ 374/5 |
| 6,082,892 A | * | 7/2000 | Adel et al. ...................... 374/123 |
| 6,108,081 A | * | 8/2000 | Holtom et al. ................. 356/301 |
| 6,127,837 A | * | 10/2000 | Yamamoto et al. ....... 324/750.05 |
| 6,151,119 A | | 11/2000 | Campion et al. |
| 6,265,890 B1 | | 7/2001 | Chacon et al. |
| 6,717,553 B2 | | 4/2004 | Sasaki et al. |
| 6,750,827 B2 | | 6/2004 | Manasson et al. |

(Continued)

FOREIGN PATENT DOCUMENTS

GB       2 223 360        4/1990
SU       1793263 A1 *     2/1993

(Continued)

OTHER PUBLICATIONS

Barker, A.S., Jr. et al., "Response Functions in the Theory of Raman Scattering by Vibrational and Polariton Modes in Dielectric Crystals," Reviews of Modern Physics, Jan. 1972, pp. 18-47, vol. 44, No. 1.

(Continued)

*Primary Examiner* — Gail Kaplan Verbitsky (74) *Attorney, Agent, or Firm* — Christopher A. Monsey (57) ABSTRACT

A method of generating a function that correlates semiconductor temperature with semiconductor lifetime including applying resonant frequency laser illumination to the semiconductor.

14 Claims, 6 Drawing Sheets

(56) References Cited

U.S. PATENT DOCUMENTS

| | | | |
|---|---|---|---|
| 6,786,637 B2 * | 9/2004 | Kuball et al. | 374/161 |
| 6,794,310 B1 | 9/2004 | Miller et al. | |
| 6,879,297 B2 | 4/2005 | Brown et al. | |
| 6,953,281 B2 * | 10/2005 | Hauenstein | 374/161 |
| 7,123,358 B2 | 10/2006 | Tuschel et al. | |
| 7,227,501 B2 | 6/2007 | Lange | |
| 7,317,194 B2 * | 1/2008 | Atzeni et al. | 250/458.1 |
| 7,352,469 B2 | 4/2008 | McGrew | |
| 7,379,030 B1 | 5/2008 | Lier | |
| 7,380,982 B2 | 6/2008 | Lohokare | |
| 7,495,823 B2 * | 2/2009 | Kanner et al. | 359/326 |
| 8,393,784 B2 * | 3/2013 | Ringermacher et al. | 374/5 |
| 2003/0161380 A1 * | 8/2003 | Hauenstein | 374/121 |
| 2004/0052296 A1 * | 3/2004 | Kuball et al. | 374/120 |
| 2004/0254769 A1 | 12/2004 | Miyairi et al. | |
| 2005/0185188 A1 | 8/2005 | McGrew | |
| 2006/0092087 A1 | 5/2006 | Lange | |
| 2006/0125706 A1 | 6/2006 | Amyotte et al. | |
| 2007/0108599 A1 * | 5/2007 | Im et al. | 257/712 |
| 2008/0129595 A1 | 6/2008 | Choi et al. | |
| 2008/0245964 A1 | 10/2008 | Miles et al. | |
| 2008/0276695 A1 | 11/2008 | Prater et al. | |
| 2009/0114805 A1 * | 5/2009 | Csutak | 250/269.1 |
| 2009/0147255 A1 | 6/2009 | Erington et al. | |
| 2010/0148049 A1 * | 6/2010 | Csutak | 250/254 |

FOREIGN PATENT DOCUMENTS

| | | |
|---|---|---|
| WO | WO 99/57542 | 11/1999 |
| WO | WO 0168271 A1 * | 9/2001 |
| WO | WO 2007/122560 | 11/2007 |

OTHER PUBLICATIONS

Behr, D. et al., "Resonant Raman scattering in GaN/(AlGa)N single quantum wells," Applied Physics Letters, Jan. 20, 1997, pp. 363-365, vol. 70, No. 3, American Institute of Physics.

Chen, G.D. et al., "Fundamental optical transitions in GaN," Applied Physics Letters, May 13, 1996, pp. 2784-2786, vol. 68, No. 20, American Institute of Physics.

Davydov, V. Yu, et al., "Phonon dispersion and Raman scattering in hexagonal GaN and AlN," Physical Review B, Nov. 15, 1998, pp. 12899-12907, vol. 58, No. 19, The American Physical Society.

Harima, H., "Properties of GaN and related compounds studied by means of Raman scattering," Journal of Physics: Condensed Matter, Sep. 12, 2002, pp. 967-993, vol. 14, Institute of Physics Publishing, UK.

Holtz, M. et al., "Composition dependence of the optical phonon energies in hexagonal $Al_xGa_{1-x}N$," Journal of Applied Physics, Jun. 15, 2001, pp. 7997-7981, vol. 89, No. 12, American Institute of Physics.

Imaino, W. et al., "Resonant Raman effect in cinnabar," Physical Review B, Jan. 15, 1980, pp. 634-642, vol. 21, No. 2, The American Physical Society.

Kovalev, D. et al., "Free exciton emission in GaN," Physical Review B, Jul. 15, 1996, pp. 2518-2522, vol. 54, No. 4, The American Physical Society.

Kudrawiec, R. et al., "Below bandgap transitions in an AlGaN/GaN transistor heterostructure observed by photoreflectance spectroscopy," Physica Status Solidi, May 29, 2006, pp. 2117-2120, (c) 3, No. 6, Wiley-VCH, Weinheim, DE.

Leroux, M. et al., "Barrier-width dependence of group-III nitrides quantum-well transition energies," Physical Review B, Jul. 15, 1999, pp. 1496-1499, vol. 60, No. 3, The American Physical Society.

Liu, M.S. et al., "Temperature dependence of Raman scattering in single crystal GaN films," Appiied Physics Letters, May 24, 1999, pp. 3125-3127, vol. 74, No. 21, American Institute of Physics.

Nuttinck, S. et al., "Direct On-Wafer Non-Invasive Thermal Monitoring of AlGaN/GaN Power HFETs Under Microwave Large Signal Conditions," $12^{th}$ Gallium Arsenide Applications Symposium [GAAS], Amsterdam, 2004, pp. 79-82, Dipartimento di Elettronica, Informatica e Sistemistica, University of Bologna, Italy.

Pokatilov, E.P. et al., "Excitons in wurtzite AlGaN/GaN quantum-well heterostrucures," Physical Review B, Mar. 19, 2008, pp. 125328-1-125328-10, vol. 77, The American Physical Society.

Sarua, A. et al., "Combined Infrared and Raman temperature measurements on device structures," CS ManTech Conference, Vancouver, CA, Apr. 24-27, 2006, pp. 179-182, CS ManTech, Beaverton, OR.

Shan, W. et al., "Strain effects on excitonic transitions in GaN: Deformation potentials," Physical Review B, Nov. 15, 1996, pp. 13460-13463, vol. 54, No. 19, The American Physical Society.

Simpson, C., "Photoluminescense and Resonant Raman Scattering in Synthetic Cinnabar" Abstract, 2 pgs., Thesis (PH.D.)-Purdue University (West Lafayette, Indiana), 1980. Source: Dissertation Abstracts International, vol. 41-06, Section: B, p. 2235.

* cited by examiner

METHOD TO MEASURE THE CHARACTERISTICS IN AN ELECTRICAL COMPONENT

STATEMENT REGARDING FEDERALLY SPONSORED RESEARCH OR DEVELOPMENT

The invention described herein includes contributions by one or more employees of the Department of the Navy made in performance of official duties and may be manufactured, used, licensed by, or for the United States Government without payment of any royalties thereon.

BACKGROUND AND SUMMARY

The present disclosure relates generally to component lifetime testing. More particularly, the present disclosure relates to temperature detection of electrical components and correlating the temperatures to component lifetime. The disclosure further discusses detecting material defects in components.

Two conventional, non-contact methods for mapping the temperature distribution of a planar electronic device are infrared (IR) thermal imaging and micro-Raman spectroscopy. The micro-Raman spectroscopy approach provides greater spatial resolution and therefore, increased accuracy.

According to one aspect of the present disclosure, a method of detecting temperature in a semiconductor is provided. The illustrative method includes the steps of: selecting a semiconductor; obtaining a virtual model of the semiconductor; selecting a material of interest present in the semiconductor; determining a resonance frequency of the material of interest; providing a laser; tuning the laser to the resonance frequency; irradiating the material of interest in the semiconductor with the laser; collecting scattered laser light emitted by the material of interest in the semiconductor; providing a spectrometer for receiving the collected laser light; and analyzing the collected laser light to determine the temperature of the material of interest in the semiconductor.

According to another aspect of the present disclosure, a method of estimating component lifetime is provided. The illustrative method includes the steps of: selecting a first semiconductor; selecting a material of interest present in the first semiconductor; obtaining a laser tuned to a resonance frequency of the material of interest; irradiating the first semiconductor with the laser; detecting laser light scattering emitted by the first semiconductor; determining a temperature of a portion of the first semiconductor; and determining a lifetime for the first semiconductor, the lifetime being a function of the determined temperature of the portion of the first semiconductor.

According to another aspect of the present disclosure, a method of generating a function that correlates semiconductor temperature with semiconductor lifetime is provided. The illustrative method includes the steps of: selecting a first semiconductor; determining a point of interest on the semiconductor; determining a material present at the point of interest on the first semiconductor; determining a resonance frequency of the material of interest; obtaining a laser tuned to the resonance frequency; placing the first semiconductor in an environment such that the point of interest on the first semiconductor has a first elevated temperature relative to normal expected operating conditions of the point of interest on the first semiconductor; irradiating the point of interest of the first semiconductor with the laser; detecting laser light scattering emitted by the point of interest on the first semiconductor; determining a temperature of the point of interest on the second semiconductor; determining a lifetime for the first semiconductor by operating the first semiconductor at the first elevated temperature until failure to generate a first data point; selecting a second semiconductor, substantially identical to the first semiconductor; placing the second semiconductor in an environment such that a point of interest on the second semiconductor has a second elevated temperature relative to normal expected operating conditions of the point of interest on the second semiconductor; the point of interest on the second semiconductor being equivalent to the point of interest on the first semiconductor; irradiating the point of interest on a second semiconductor with the laser; detecting laser light scattering emitted by the point of interest on the second semiconductor; determining a temperature of point of interest on the second semiconductor; determining a lifetime for the second semiconductor by operating the second semiconductor until failure to generate a second data point; and conducting a mathematical procedure to generate a best-fitting curve for the set of points containing the first data point and the second data point.

According to another aspect of the present disclosure, an illustrative method of detecting defects in a semiconductor includes the steps of: obtaining a semiconductor; selecting a material of interest present in the semiconductor; determining a resonance frequency of the material of interest; obtaining a laser tuned to the resonance frequency; raster irradiating the semiconductor with the laser; collecting scattered laser light emitted by the material of interest in the semiconductor; analyzing the collected laser light to determine an observed temperature map of the semiconductor; comparing the observed temperature map to an expected temperature profile; and identifying differences between the observed temperature map and the expected temperature profile and noting the locations of differences as potential defect locations.

According to another aspect of the present disclosure, a method of detecting temperature in a material is provided. The illustrative method includes the steps of: selecting a material; obtaining a virtual model of the material; determining a resonance frequency of the material; obtaining a laser tuned to the resonance frequency; irradiating the material with the laser; collecting scattered laser light emitted by the material; and analyzing the collected laser light to determine the temperature of the material.

Additional features of the present disclosure will become apparent to those skilled in the art upon consideration of the following detailed description of the presently perceived best mode of carrying out the disclosure.

BRIEF DESCRIPTION OF THE DRAWINGS

The detailed description of the drawings particularly refers to the accompanying figures in which.

DETAILED DESCRIPTION OF THE DRAWINGS

Figure 1:
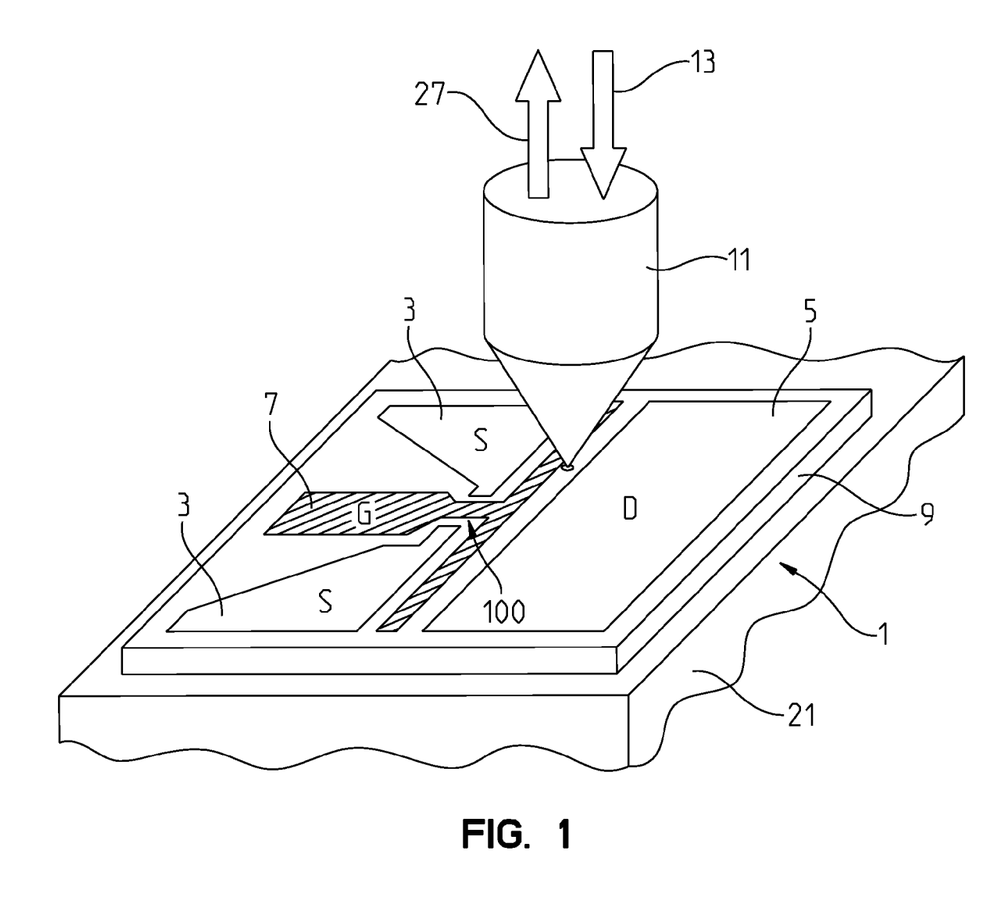
FIG. 1 is a partial perspective view of an illustrative arrangement for making micro-Raman scattering measurements.
Figure 2:
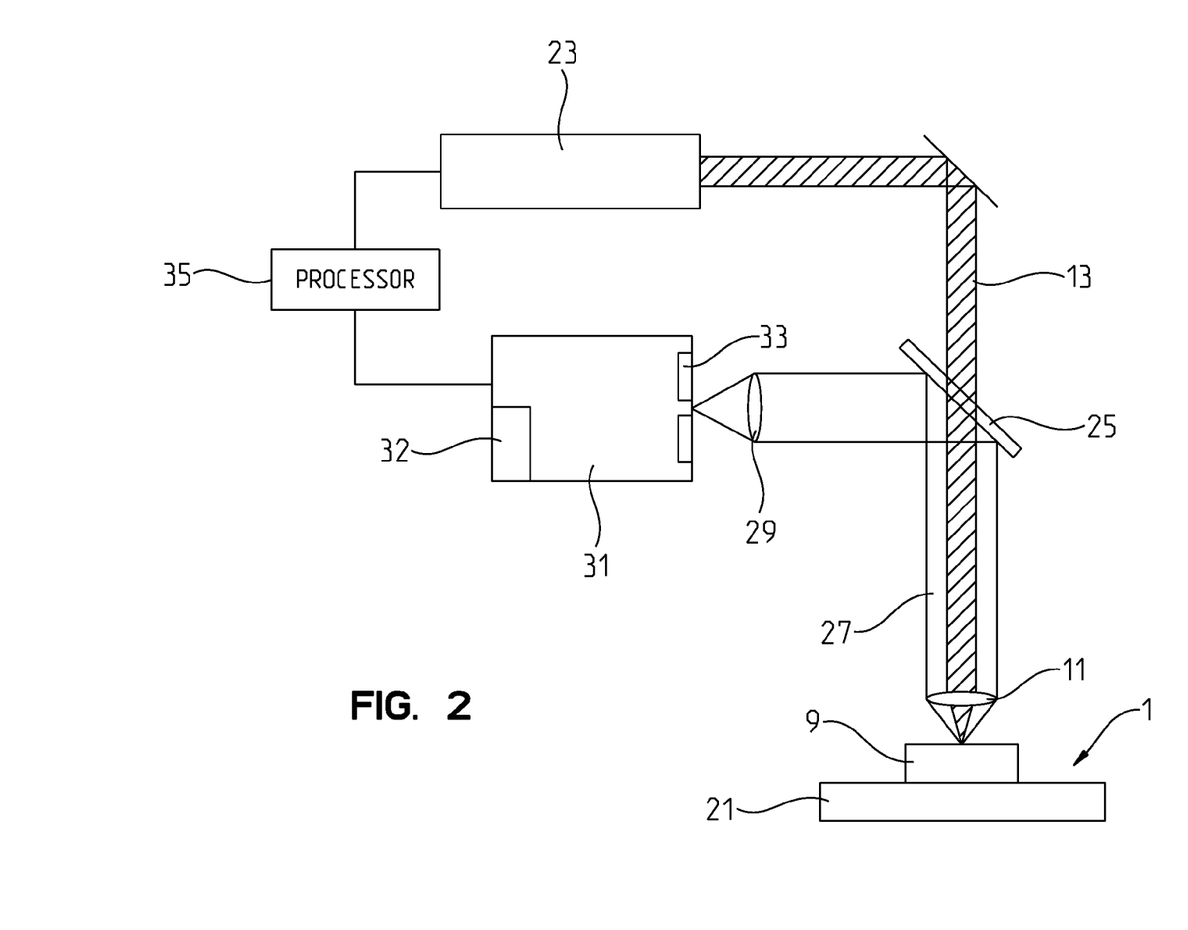
FIG. 2 is a schematic side view of the arrangement of FIG. 1.

FIGS. 1 and 2 show an arrangement for making micro-Raman scattering measurements on a heterostructure field-effect transistor (HFET) 1. While various semiconductors will be discussed herein for illustrative purposes, it should be appreciated that the various methods and devices are envisioned to be used with a variety of materials, including but not limited to wide band gap semiconductors, heterostructures, quantum wells, and HFET's.

The arrangement includes laser 23 (that generates laser beam 13), laser focusing element (lens) 11, beam splitter 25 (that collects scattered light 27), lens 29, base plate 21, and spectrometer 31. HFET 1 includes source 3, drain 5, gate 7, and substrate 9. Spectrometers are known instruments used to measure properties of light, often for identifying materials. In the illustrative embodiment, spectrometer 31 includes linear photodetector array 32 and entrance slit 33.

Atoms of HFET 1 form a lattice with adjacent atoms. Raman spectroscopy involves irradiating a sample, such as the shown HFET 1, with laser beam 13 and measuring the light scattered from the volume illuminated by laser beam 13 (also referred to as Raman scattering). Scattering is the process whereby the applied light is re-radiated from the volume of the illuminated material (HFET 1 in this example) in directions different than the original direction of the illuminating light. The irradiated material of HFET 1 is considered transparent to the laser light in that the laser light is able to penetrate into the material to a necessary depth and subsequently be scattered therefrom. Accordingly, as used herein "transparent" refers to this quality, and not the traditional use of "transparent" meaning "able to be seen through without distortion."

The energy of the irradiation couples with the vibrational energy, or energies, of the atoms in the crystal lattice of HFET 1. This coupling is a non-linear interaction of the laser light with the lattice vibrations of the sample (periodic oscillations of the atoms about their equilibrium positions) and causes the generation of sideband frequency emission signals from inelastic scattering. The sidebands of scattered light are characteristic of the crystal structure of the sample being irradiated. The inelastically scattered light having energy lower than that provided by the laser is called Stokes scattering. Scattered light having higher energy than the laser is called anti-Stokes scattering. Both Stokes and anti-Stokes scattering are examples of a Raman shift.

Quantized lattice vibrations are called Phonons. In Stokes scattering, a phonon is generated, and in anti-Stokes scattering, a phonon is annihilated. Depending on the crystal structure of the sample, there can be one or several characteristic phonons. Raman scattering permits two methods of measuring the temperature of a semiconductor: phonon shifts due to thermal expansion and intensity ratio of Stokes and anti-Stokes scattering.

Micro-Raman spectroscopy uses a microscope to focus the laser onto the sample and collect the scattered light. The use of laser 23 and lens 11 allows a small spot size and therefore a resolution of 1 micro-meter. HFET 1 is placed on temperature-controlled base plate 21. The laser beam spot is rastered over the surface of HFET 1. Raster Scanning, by which HFET 1 is "rastered" is a method of scanning in which the scanning spot moves along a network of parallel lines, either from side to side or top to bottom to effectively cover the entire area being examined. One analog to raster scanning is the way in which one reads written English, by moving from left to right across a line, and then moving down to the next line and repeating the process.

As the laser beam spot is rastered across HFET 1, the material of HFET 1 inelastically scatters some of the light back within the acceptance cone of lens 11. Scattered light 27 is collected and collimated by lens 11, reflected by beam splitter 25 onto lens 29 which directs scattered light 27 onto entrance slit 33 of spectrometer 31. Spectrometer 31 disperses the spectrum of scattered light 27 onto linear photodetector array 32. Linear photodetector array 32 detects wavelength-dependent intensity of scattered light 27. The detected wavelength intensity is subsequently processed to produce a spectrum of light intensity as a function of wavelength or wave number.

Micro-Raman spectrometer 31 collects a spectrum and determines the Raman shift for the spectral features observed by either a phonon shift method or an intensity ratio method. Using a phonon shift method, the experimentally-measured Raman shift as a function of temperature is fit into the equation:

$$\omega(T) = \omega_0 - \frac{A}{e^{B(\hbar\omega_0/kT)} - 1},$$

where $\omega_0$ is the phonon frequency at very low temperatures, $\hbar$ is Planck's constant divided by $2\pi$, k is Boltzmann's constant, T is the absolute temperature, and A and B are material-dependent parameters.

Using the intensity ratio method for a particular phonon, the intensity of anti-Stokes scattering divided by the intensity of Stokes scattering is given by:

$$\frac{I_{AS}(\omega_k)}{I_S(\omega_k)} = e^{(-\hbar\omega_k/kT)},$$

where $I_{AS}(\omega_k)$ is the intensity of the anti-Stokes scattering involving the k-th phonon having frequency $\omega_k$, and $I_S(\omega_k)$ is the intensity of the Stokes scattering for the same phonon. By so fitting according to one of the above methods (i.e., phonon shift or intensity ratio), a processor 35, maps the temperature of the various parts of HFET 1. Accordingly, the temperature determination is dependent upon accurate measuring of the phonon frequency shift or the presence and accurate measuring of the anti-Stokes and Stokes scattering.

By so fitting according to one of the above methods (i.e., phonon shift or intensity ratio), the temperature of the various parts of HFET 1 can be mapped. Accordingly, the temperature determination is dependent upon accurate measuring of the phonon frequency shift or the presence and accurate measuring of the anti-Stokes and Stokes scattering.

By choosing the frequency of applied laser 23 to be a resonant frequency of the material being observed (HFET 1), a greater intensity response can be generated for both the anti-Stokes and Stokes scattering relative to a similarly supplied laser intensity at a non-resonant frequency.

Figure 3:
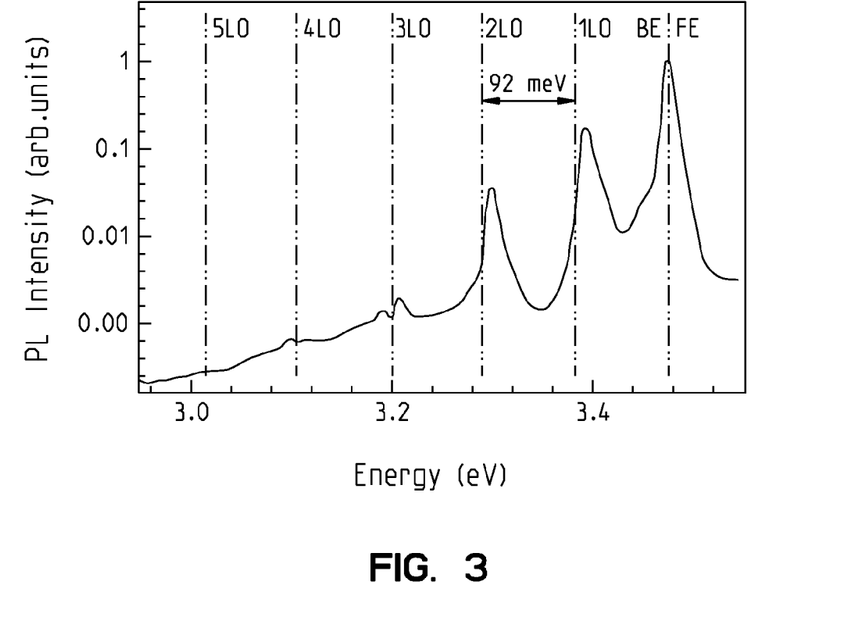
FIG. 3 is a photoluminescence spectra of bulk GaN which can be used to tune the arrangement of FIG. 1.
Figure 4:
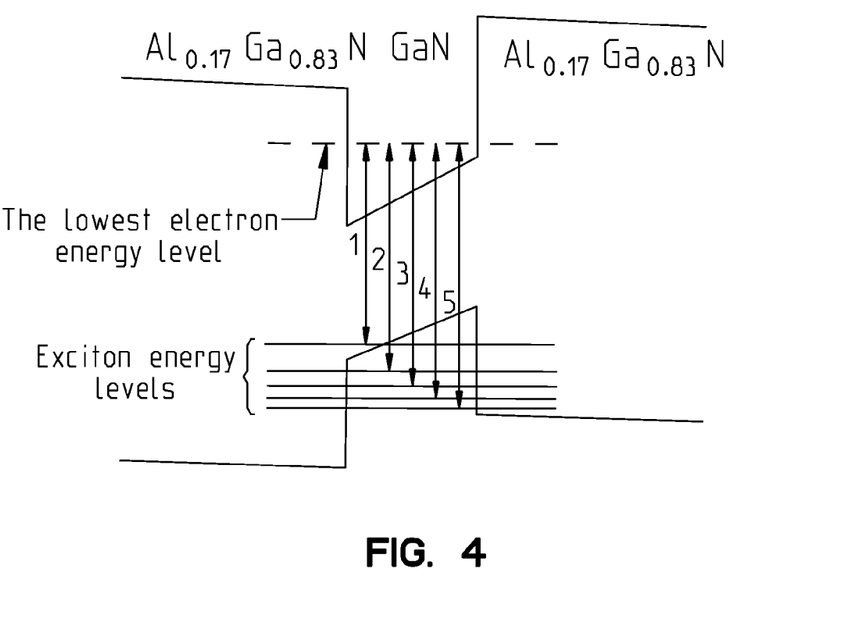
FIG. 4 is a chart of the five lowest energy levels of a heterostructure which can be used to tune the arrangement of FIG. 1.
Figure 5:
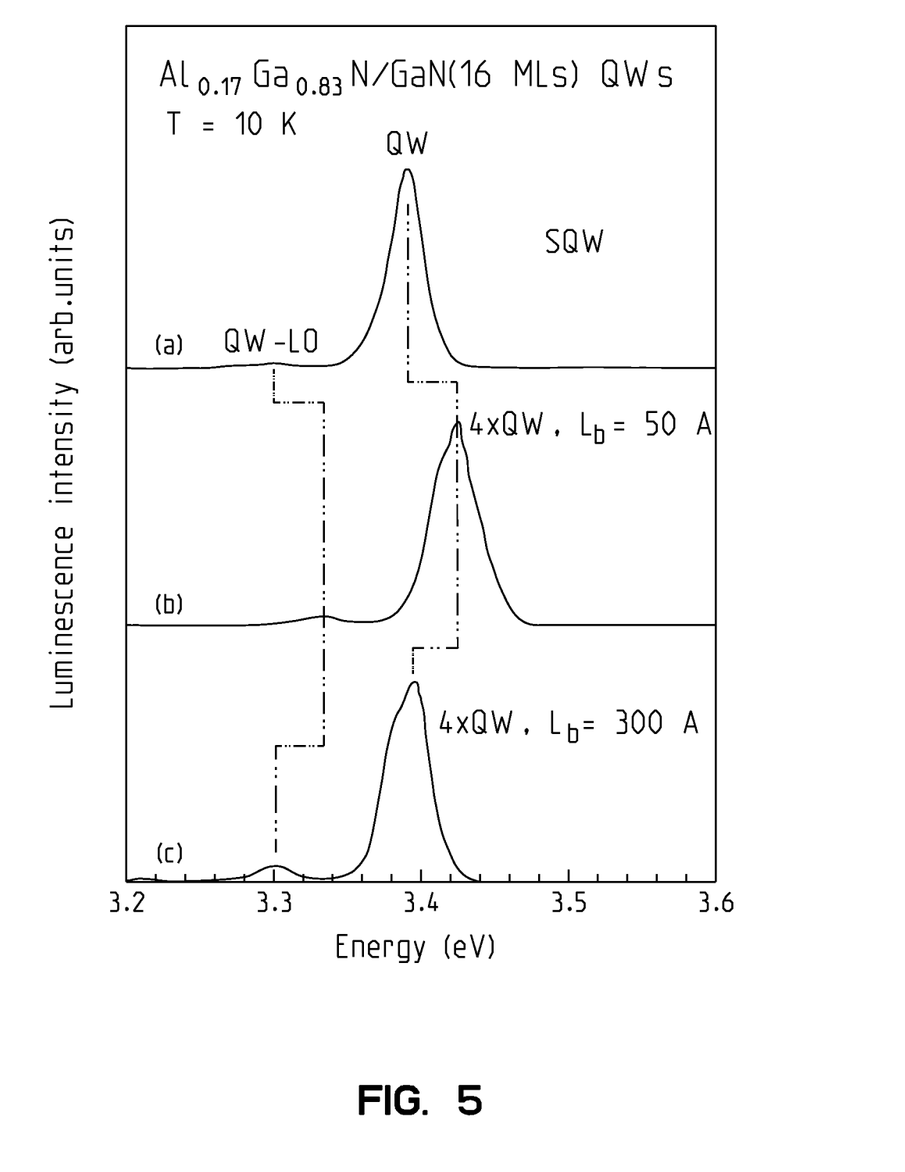
FIG. 5 is a photoluminescence spectra of quantum wells which can be used to tune the arrangement of FIG. 1.

The resonant frequencies can be located various ways. One such way is via photoluminescence (PL). PL involves irradiating a sample with light having energy greater than the band gap of the semiconductor material and observing the photons emitted therefrom. As an example, FIG. 3 shows the PL spectra of bulk GaN at a Temperature of 50K. Emission from free exciton (FE) and bound exciton (BE) states near the band gap occurs near ~3.48 eV. PL peaks also occur at multiple phonon energies (92 meV, or 742 cm$^{-1}$.) below the near-band-edge emission. While the energy levels for an AlGaN/GaN/AlGaN quantum well (QW) are not exactly the same as that for the triangular quantum well of an AlGaN/GaN heterojunction, they are similar. FIG. 4 shows the energy levels for an $Al_{0.17}Ga_{0.83}N$/GaN MQW heterostructure. PL emission for a single quantum well (SQW) and the multiple quantum wells (MQWs) of the structure shown in FIG. 4 is shown in FIG. 5. Peaks in photon emission, having greater intensity, are seen at the resonant frequencies.

When the laser energy in a micro-Raman measurement is coincident in energy with these peaks in PL emission, greater scattering signal results. Thus resonant excitation allows for measuring the scattering intensity with improved signal-to-noise ratios and thus permitting a better estimate of the temperatures present in HFET 1.

Through increased accuracy in temperature determination, this more reliable data is used in calculations used to determine reliability of HFET 1. Additionally, scanning at resonant frequencies is used for increased accuracy photoluminescence mapping of a device to determine such parameters as alloy composition, quantum well and impurity level energies, impurity distribution, doping levels, and point and line defect existence and concentrations. Furthermore, scanning at resonant frequencies can be used in micro-Raman temperature mapping of a device to determine strain from heterostructures or crystal lattice structure defects. Where the micro-Raman mapping provides a temperature map of the device that differs substantially from the expected temperature map, as determined from a finite element model, discussed below, such differences are investigated as potential defect locations. Defects at these locations may be the cause of subsequent device failure.

Additionally, mapping allows the temperatures of the various parts of HFET 1 to be observed and relationships defined for the temperatures of the parts of HFET 1. For example, mapping HFET 1 allows a relationship to be determined for the temperatures of channel 100 and base plate 21. Thus, by knowing this relationship and knowing the temperature of base plate 21, the temperature of channel 100 can be determined without having to actually measure the temperature of channel 100.

For any semiconductor being examined, such as HFET 1, a finite element model (computerized virtual model) or other means of determining a failure point such as observing failure points may be utilized. To create this model, design and materials information is provided to a modeling program. Such suitable modeling programs include but are not limited to ANSYS and COSMOL Multiphysics. Once the relevant data is assembled, the performance of the semiconductor can be modeled. Various environmental conditions in which the semiconductor operates can be input into the modeling program to output a temperature map or other report indicative of semiconductor operation for the given environmental conditions. Such a temperature map shows the expected temperatures of the parts of the semiconductor for the given input conditions (semiconductor design as well as applied voltages and ambient conditions). The temperature map shows the layout of the semiconductor and shows the temperatures of the various parts thereof.

Figure 6:
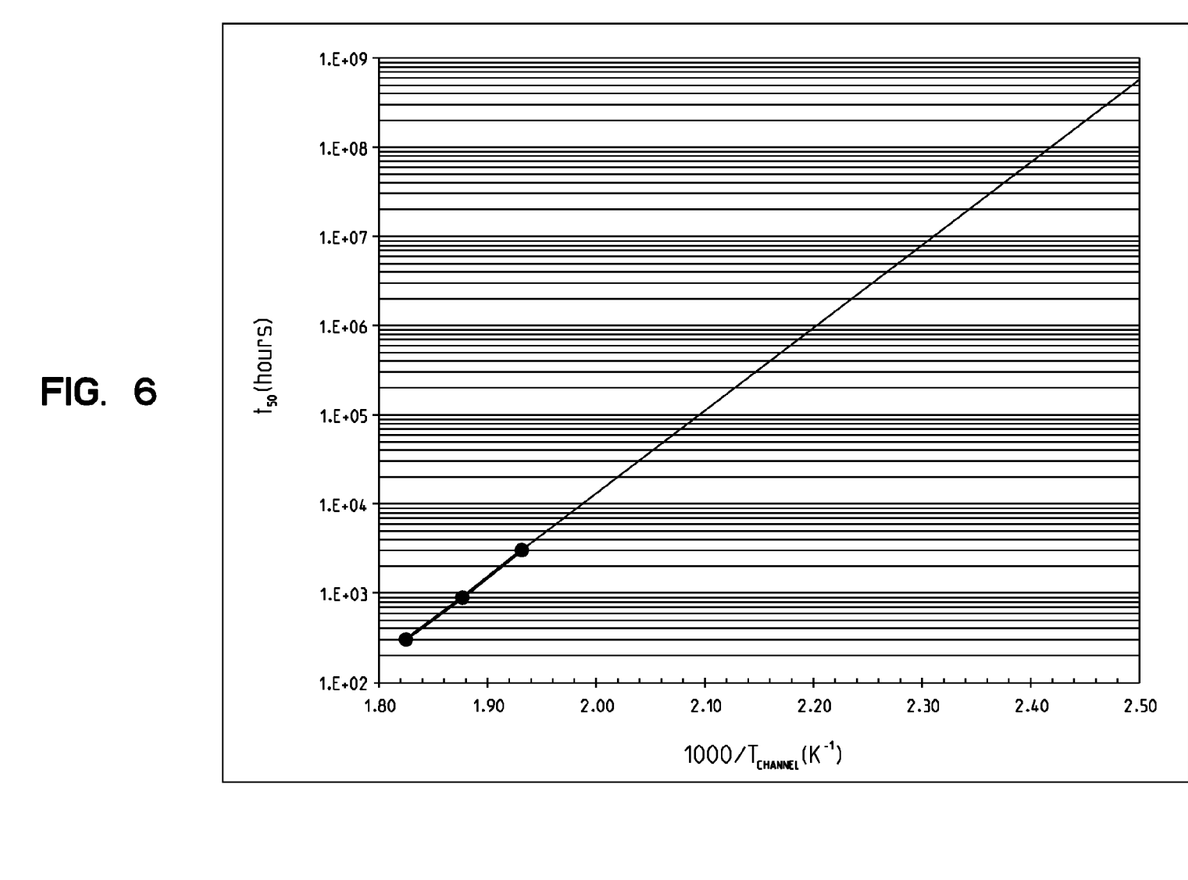
FIG. 6 is a graph showing expected semiconductor lifetime at a range of temperatures, three temperatures shown in this example, that is generated from the testing done with the arrangement of FIG. 1.

Once the failure point is determined by the use of the model or otherwise, this point then becomes a point of interest in a lifetime analysis. In HFET 1, point of interest 100, FIG. 1, is at the channel proximate gate 7. A first HFET 1 is operated at a first elevated temperature until failure. A second HFET 1 is then operated at a second elevated temperature until failure. A third HFET 1 is then operated at a third elevated temperature until failure. If desired, further elevated temperature testing to failure is conducted. Before or during each of the failure tests, the above-described micro-Raman mapping is performed to gain accurate readings of the temperature at point of interest 100. With the temperatures and lifetime data, a least squared fit approximation is applied to the data points to achieve a function that approximates the observed data and to achieve a graph showing expected semiconductor lifetime at a range of temperatures, as shown in FIG. 6. It should be appreciated that an actual graph need not be created, but rather a function can be generated from the data points to yield a functional relationship between operating temperature at point 100 and expected lifetime. It should be appreciated that while the first HFET 1, second HFET 1, and third HFET 1 are all discussed above as being singular HFET's 1, it is common that first, second, and third HFET's 1 are actually large numbers of HFET's 1. In such embodiments, many HFET's 1 are run to failure at each of the elevated temperatures. The time to failure that is used is the time that it takes 50% of the samples being tested to fail or degrade to a specified level this time is denoted as $t_{50}$ (hours).

A working HFET 1, not a HFET 1 operated to failure, is then placed in an environment designed to approximate the environment where HFET 1 will be expected to operate. Micro-Raman mapping is applied to HFET 1 to obtain a temperature at point of interest 100 in the expected operating environment. The temperature of point 100 is then compared to the created graph, FIG. 6, such that an expected lifetime is determined. It should be appreciated that the HFET's 1 or other semiconductors used in the testing are all substantially identical to each other. In other words, the semiconductors are identical except for any manufacturing defects or variances.

Figure 7:
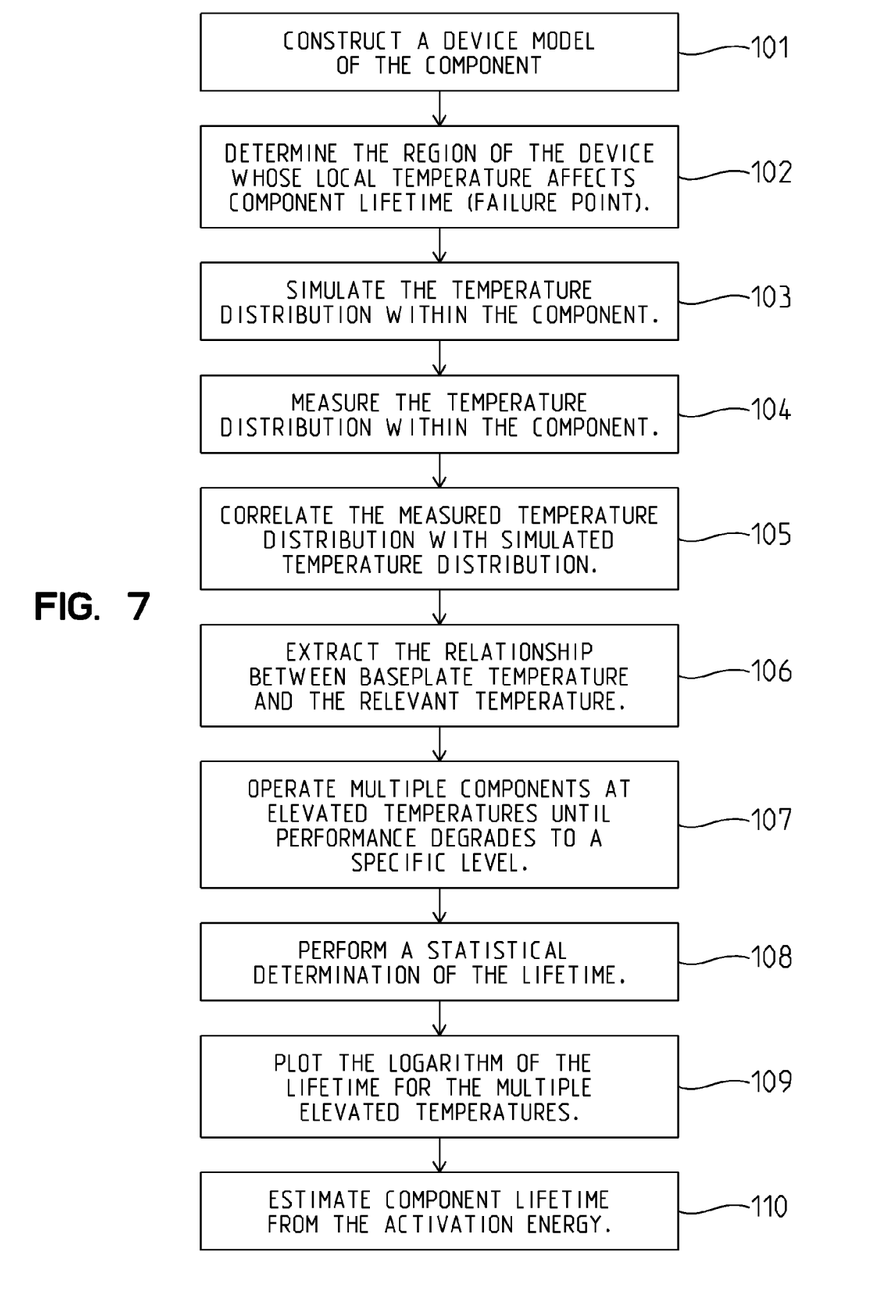
FIG. 7 is a flow chart showing the steps of an illustrative method for measuring characteristics in an electrical component that utilizes the arrangement of FIGS. 1 and 2 and uses the data contained in FIGS. 3-6.

Thus, an illustrative process for using resonant micro-Raman scattering for temperature measurement for component lifetime determination includes the following steps outlined in FIG. 7.

Step 101: Construct a device model of the component, such as HFET 1 of FIG. 1. Illustrative items included in the model are the following:

a. Materials (i.e., GaAs, AlGaAs, GaN, AlGaN, SiC, metals, insulators, protective coatings, adhesives, etc.).

b. Thermal properties (thermal conductivity, interface thermal conductances).

c. Electrical properties (electrical conductivity, carrier type and concentrations).

d. Dimensions (layer thicknesses, lateral dimensions).

e. Interdependencies of items a-d in the model.

Step 102: Determine the region of the device whose local temperature affects component lifetime (failure point). In an HFET, the relevant region is illustratively channel 100, thus channel temperature $T_{channel}$ is the relevant temperature. In a bipolar device, the relevant region is illustratively the junction, thus junction temperature $T_{junction}$ is the relevant temperature.

Step 103: Using the device model, simulate the temperature distribution within the various regions of the component for given base plate temperatures under given operating conditions. A finite element model is often used to accomplish this simulation. Since the gate lengths of microwave semiconductor devices are often only a fraction of a micrometer ($10^{-6}$ m), the spatial resolution of the model for temperature near the gate is chosen to be able to accurately model the gate.

Step 104: Measure the temperature distribution within several components under identical operating conditions, such as bias conditions and signal input power levels. For sub-micrometer gate lengths, the spatial resolution to which the temperature near the gate can be determined is chosen with the knowledge of the gate size and the resolution needed to achieve accuracy. The method of this disclosure is used to make accurate measurements of this temperature distribution.

Step 105: Correlate the measured temperature distribution with simulated temperature distribution.

Step 106: Extract the relationship between base plate 21 temperature ($T_{baseplate}$) and the relevant temperature (such as $T_{channel}$) for all operating conditions of interest. Operating conditions, such as applied bias voltages and currents, are accounted for in the relationship between relevant temperature and base plate 21 temperature, due to possible self-heating effects.

Step 107: Operate multiple components at elevated base plate temperatures until performance degrades to a specified level. Illustratively, in FIG. 6, three elevated base plate temperatures are used. The number of components operated at each elevated temperature is determined by the expected lifetime.

Step 108: Perform a statistical determination of the lifetime. The accuracy of the lifetime estimate is greater when a larger number of components are tested. One typical lifetime parameter is the time for half of the components to have degraded to the specified level; this time is denoted $t_{50}$ (hours).

Step 109: Plot the logarithm of the lifetime $t_{50}$ (hours) for the multiple elevated temperature conditions as a function of reciprocal critical temperature (i.e., $T_{channel}$). An example of this plot is shown in FIG. 6. Since the relationship between $t_{50}$ and $T_{channel}$ is given by:

$$t_{50} = t_0 e^{E_A/kT_{channel}}$$

the data will fall on a straight line, given by the relation:

$$\ln t_{50} = \left(\frac{E_A}{k}\right)\frac{1}{T_{channel}} + \ln t_0,$$

using either graphical or least-squares methods, a value for activation energy $E_A$ can be determined.

Step 110: From the activation energy $E_A$ and the relationship between $T_{baseplate}$ and $T_{channel}$, estimates of component lifetime can be made.

Component lifetime estimates can then be used to qualify component for various uses. More specifically, a circuit designer can specify a required component lifetime based on the use in which the circuit will be employed. By performing the above steps, components generally, and components of a particular production run can be tested and qualified for specific uses.

Although the disclosure has been described in detail with reference to certain preferred embodiments, variations and modifications exist within the spirit and scope of the disclosure as described and defined in the following claims.

The invention claimed is:

1. A method of estimating component lifetime including the steps of:
    selecting a first semiconductor;
    selecting a material of interest present in the first semiconductor;
    obtaining a laser tuned to a resonance frequency of the material of interest operable to increase Stokes and anti-Stokes scattering arising from interactions between laser light from said laser and said material of interest;
    irradiating the first semiconductor with the laser;
    detecting laser light scattering emitted by the first semiconductor;
    determining a temperature of a portion of the first semiconductor; and
    determining a lifetime for the first semiconductor, the lifetime being a function of the determined temperature of the portion of the first semiconductor;
    wherein said laser tuned to said resonance frequency is tuned based on a first and second property of the material of interest, wherein said first property comprises a vibrational property associated with lattice vibrations of said material of interest stimulated by said laser at said resonance frequency and said second property comprising an energy level of said material of interest associated with said scattering of said laser's output incident on said material of interest at said resonance frequency.

2. The method of claim 1, wherein the step of irradiating the first semiconductor includes rastering across the semiconductor.

3. The method of claim 2, wherein the step of determining a temperature includes generating a temperature map over a surface of said semiconductor device.

4. The method of claim 3, wherein the step of determining a lifetime includes determining the point on the temperature map that is most likely to induce failure.

5. The method of claim 3, wherein the temperature map provides for the establishing of temperature relationships between a point of interest in the first semiconductor and a base plate in contact with the first semiconductor.

6. The method of claim 1, wherein the step of determining a lifetime includes comparing the determined temperature to a graph that relates operating temperature to lifetime.

7. The method of claim 6, further including the step of creating a temperature-to-lifetime graph, the creating step including the steps of:
    placing a second semiconductor in an environment such that a point of interest on the second semiconductor has an elevated temperature relative to normal expected operating conditions; the second semiconductor being similarly constructed as the first semiconductor;
    irradiating a second semiconductor with the laser;
    detecting laser light scattering emitted by the second semiconductor;
    determining a temperature of a portion of the second semiconductor; and
    determining a lifetime for the second semiconductor by operating the second semiconductor until failure.

8. The method of claim 1, wherein said energy level of said material of interest is determined based on a separation of energy states characteristic within said material, said laser's wavelength is tuned to substantially match said separation of energy states to satisfy a condition of said resonance frequency associated with said material of interest.

9. A method of generating a function that correlates semiconductor temperature with semiconductor lifetime, the method including the steps of:
    selecting a first semiconductor;
    determining a point of interest on the semiconductor;
    determining a material present at the point of interest on the first semiconductor;
    determining a resonance frequency of the material of interest operable to increase Stokes and anti-Stokes scattering arising from interactions between laser light from a laser and said material of interest;
    obtaining said laser tuned to the resonance frequency;
    placing the first semiconductor in an environment such that the point of interest on the first semiconductor has a first elevated temperature relative to normal expected operating conditions of the point of interest on the first semiconductor;

irradiating the point of interest of the first semiconductor with the laser;

detecting laser light scattering emitted by the point of interest on the first semiconductor;

determining a temperature of the point of interest on the first semiconductor;

determining a lifetime for the first semiconductor by operating the first semiconductor at the first elevated temperature until failure to generate a first data point;

selecting a second semiconductor, substantially identical to the first semiconductor;

placing the second semiconductor in an environment such that a point of interest on the second semiconductor has a second elevated temperature relative to normal expected operating conditions of the point of interest on the second semiconductor; the point of interest on the second semiconductor being equivalent to the point of interest on the first semiconductor;

irradiating the point of interest on a second semiconductor with the laser;

detecting laser light scattering emitted by the point of interest on the second semiconductor;

determining a temperature of the point of interest on the second semiconductor;

determining a lifetime for the second semiconductor by operating the second semiconductor until failure to generate a second data point; and conducting a mathematical procedure to generate a best-fitting curve for the set of points containing the first data point and the second data point;

wherein said determining said resonance frequency of the material of interest based on a first and second property of the material of interest, wherein said first property comprises a vibrational property associated with lattice vibrations of said material of interest stimulated by said laser at said resonance frequency and said second property comprising an energy level of said material of interest associated with said scattering of said laser's output incident on said material of interest at said resonance frequency.

10. The method of claim 9, further including the steps of:
selecting a third semiconductor, substantially identical to the first semiconductor;
placing the third semiconductor in an environment such that a point of interest on the third semiconductor has a third elevated temperature relative to normal expected operating conditions of the point of interest on the third semiconductor; the point of interest on the third semiconductor being equivalent to the point of interest on the first semiconductor;
irradiating the point of interest on a third semiconductor with the laser;
detecting laser light scattering emitted by the point of interest on the third semiconductor;
determining a temperature of point of interest on the third semiconductor;
determining a lifetime for the third semiconductor by operating the third semiconductor until failure to generate a third data point; and
the step of conducting a mathematical procedure includes finding the best-fitting curve to the set of points containing the first data point, the second data point, and the third data point.

11. The method of claim 9, wherein the first elevated temperature is different from the second elevated temperature.

12. The method of claim 9, further including the steps of:
selecting a fourth semiconductor, substantially identical to the first semiconductor;
placing the fourth semiconductor in an environment such that a point of interest on the fourth semiconductor experiences an environment equivalent to its normal expected operating conditions; the point of interest on the fourth semiconductor being equivalent to the point of interest on the first semiconductor;
irradiating the point of interest on the fourth semiconductor with the laser;
detecting laser light scattering emitted by the point of interest on the fourth semiconductor;
determining a temperature of the point of interest on the fourth semiconductor;
determining a lifetime for the fourth semiconductor by comparing the temperature of the point of interest on the fourth semiconductor to the best-fitting curve generated from the set of points.

13. The method of claim 9, wherein the step of determining the temperature of a point of interest on the first semiconductor includes obtaining a temperature map that provides for the establishing of temperature relationships between the point of interest in the first semiconductor and a base plate in contact with the first semiconductor.

14. The method of claim 4, further comprising repeating said steps of said method for a plurality of ambient temperatures or temperatures at which said semiconductor device self-heats in an operating condition and thereby generate additional data points on a graph showing a graphical relationship of data associated with said ambient temperatures or said temperatures at which said device self heats versus said lifetime data points.

* * * * *